United States Patent [19]

Gaertner et al.

[11] 4,063,922

[45] Dec. 20, 1977

[54] N-(2-HYDROXYALKYL) DERIVATIVES OF N-PHOSPHONOMETHYLGLYCINE FOR TREATMENT OF SUGARCANE

[75] Inventors: Van R. Gaertner, Ballwin; Philip C. Hamm, Glendale, both of Mo.

[73] Assignee: Monsanto Company, St. Louis, Mo.

[21] Appl. No.: 714,053

[22] Filed: Aug. 13, 1976

[51] Int. Cl.$^2$ .............................................. A01N 9/36
[52] U.S. Cl. ...................................................... 71/86
[58] Field of Search ............................................ 71/86

[56] References Cited

U.S. PATENT DOCUMENTS

| | | | |
|---|---|---|---|
| 3,453,301 | 7/1969 | Uhing | 71/86 X |
| 3,455,675 | 7/1969 | Irani | 71/86 |
| 3,556,762 | 1/1971 | Hamm et al. | 71/86 |
| 3,799,758 | 3/1974 | Franz | 71/86 |
| 3,835,000 | 9/1974 | Frazier et al. | 204/78 |
| 3,853,530 | 12/1974 | Franz | 71/76 |
| 3,910,969 | 10/1975 | Franz | 260/397.7 R |
| 3,933,946 | 1/1976 | Gaertner | 71/86 X |

Primary Examiner—Joseph Paul Brust
Attorney, Agent, or Firm—Arnold H. Cole; Donald W. Peterson

[57] ABSTRACT

Certain N-(2-hydroxyalkyl) derivatives of N-phosphonomethylglycine have been found to be useful in the treatment of sugarcane plants to increase their sucrose content.

11 Claims, No Drawings

N-(2-HYDROXYALKYL) DERIVATIVES OF N-PHOSPHONOMETHYLGLYCINE FOR TREATMENT OF SUGARCANE

This invention relates to the use of certain N-(2-hydroxyalkyl) derivatives of N-phosphonomethylglycine for the treatment of sugarcane plants to increase their sucrose content.

U.S. Pat. No. 3,455,675 teaches the use of certain aminophosphonate compounds as herbicides for the destruction of undesired plants. These compounds require the presence of three acid groups attached to the nitrogen atom, each attachment being through an alkylene (or methylene) bridge. One or two of such acid groups must be phosphonic acid, and the remaining group or groups must be carboxylic acid (acetic acid). In U.S. Pat. No. 3,556,762 this same class of compounds is shown to be useful in the treatment of sugarcane to increase its sucrose content. Further, U.S. Pat. No. 3,799,758 teaches that N-phosphonomethylglycine, and certain esters, amides and salts thereof, are useful as herbicides for the destruction of undesired plants. All of these compounds must contain a hydrogen atom on the nitrogen. The same class of compounds, also including some N-acyl derivatives, are shown in U.S. Pat. No. 3,853,530 to have utility in the treatment of sugarcane plants to increase sucrose content. Most recently, U.S. Pat. No. 3,910,969 shows that N-phenylsulfonamido derivatives of N-phosphonomethylglycine are useful in the treatment of sugarcane to increase sucrose content.

In accordance with the present invention, it has been found that certain N-(2-hydroxyalkyl) derivatives of N-phosphonomethylglycine, along with esters and salts thereof, can be employed to increase the sucrose content of sugarcane plants. Such derivatives may be represented by the formula

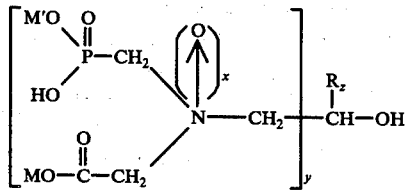

wherein $x$ is selected from zero and one, $y$ is selected from one and two, $z$ is selected from zero and one, the sum of $y + z$ is two, R is selected from hydrogen, methyl, ethyl, hydroxymethyl and lower alkoxymethyl, M is selected from hydrogen, lower alkyl and alkali metal, and M' is selected from hydrogen, lower alkyl, phenyl and alkali metal. As employed herein, lower alkyl designates the straight and branched chain saturated aliphatic hydrocarbon radicals having from one to four carbon atoms.

U.S. Pat. No. 3,835,000 discloses N-(2-hydroxyethyl)-N-phosphonomethylglycine as a starting material in a chemical process. Said patent describes a general method for preparing this starting material in Column 4. Another method for preparing compounds of this invention involves the reaction of a suitable epoxide with an alkali metal salt of N-phosphonomethylglycine.

In those instances where $y$ is one, the two reactants can be employed in equimolar amounts although an excess of epoxide may be used to assist in driving the reaction to completion. In those instances where $y$ is two, the starting salt is employed in approximately a 2:1 molar ratio relative to the epoxide. The products obtained by the above reactions are in salt form, and, if desired, can be acidified by known procedures to give the corresponding free acids. These acids are stable at room temperatures, but will lactonize as temperatures are elevated. The N-oxides of said products are obtained by reaction with a suitable oxidizing agent.

The reaction is generally carried out at room temperature or below, and external cooling may be necessary due to exothermic temperature increases. The reaction should be carried out at a pH in the range of about 6 to 9.

The examples which follow will serve to further illustrate the preparation of specific individual compounds of the present invention.

EXAMPLE 1

The disodium salt of N-phosphonomethylglycine is prepared by treating a slurry of 16.9 grams (0.10 mole) of N-phosphonomethylglycine in 30 ml. of water with 16 grams (0.20 mole) of 50% aqueous sodium hydroxide. The hot solution is stirred and cooled in an ice bath to 5–10° C.

To the disodium salt solution is added 8.1 grams (0.11 mole) of glycidol. The solution is then allowed to stir and warm overnight in the melting ice bath. To complete the reaction, a 2.0 gram portion of glycidol is added, and the solution is stirred at 22° C. The solution is allowed to stand for several days and is then rotoevaporated to dryness. The solid is then redried over potassium hydroxide pellets in a vacuum desiccator below 1 mm. Hg. There is obtained the disodium salt of N-(2,3-dihydroxy-1-propyl)-N-phosphonomethylglycine as a white, brittle foamed glass.

EXAMPLE 2

To a solution of the disodium salt of N-phosphonomethylglycine, prepared as in Example 1 above, there is added 4.6 grams (0.05 mole) of epichlorohydrin, and the solution is allowed to stir overnight at a temperature of 20–25° C. The solution is left standing for several days with additions of sufficient sodium hydroxide solution to keep a phenolphthalein indicator strongly pink. An additional 2.0 grams of epichlorohydrin is added to complete the reaction, and the solution is allowed to stand for several more days with additions of sodium hydroxide as before. The solution is then rotoevaporated to dryness, and the residue is redried over potassium hydroxide pellets. The product, obtained as a white foamed glass, is the tetrasodium salt of N,N'-di(carboxymethyl)-N,N'-di(phosphonomethyl)-1,3-diamino-2-propanol.

EXAMPLE 3

To 2.7 grams (0.01 mole) of ethyl N-phenoxyphosphinyl methylglycinate in 10 ml. of water is added 0.8 gram (0.01 mole) of 50% aqueous sodium hydroxide. The solution is shaken and cooled in a pressure bottle. It is then treated with 0.5 gram (0.0115 mole) of ethylene oxide, allowed to warm to 20–25° C., and then allowed to stand overnight. The resultant solution is rotoevaporated to dryness, and the residue is redried over potassium hydroxide pellets. The product, obtained as a friable, white glass, is the monosodium salt of N-(2-hydroxyethyl)-N-(hydroxyphenoxyphosphinylmethyl)glycine in the hemihydrate form. Elemental analysis shows 41.09% carbon, 5.05% hydrogen and 9.70% phosphorus as against calculated values of 41.26%, 5.04% and 9.67% for $C_{11}H_{15}NaNO_6P \frac{1}{2} H_2O$.

EXAMPLE 4

To 8.5 grams (0.05 mole) of N-phosphonomethylglycine in 30 grams of water is added 8.0 grams of 50% aqueous sodium hydroxide. The solution is cooled and 3.6 grams (0.05 mole) of 1,2-butylene oxide is added. This solution is rotated on a polymer wheel overnight. Additional amounts of 1,2-butylene oxide are added until no N-phosphonomethylglycine is detected in the solution, and unreacted 1,2-butylene oxide is then extracted with ethyl ether and benzene. The solution is rotoevaporated to dryness, and the residue is redried over sodium hydroxide pellets. The product, obtained as brittle white foam, is the disodium salt of N-(2-hydroxy-1-butyl)-N-phosphonomethylglycine. Elemental analysis shows 30.68% carbon, 5.48% hydrogen, 4.70% nitrogen and 10.20% phosphorus as against calculated values of 29.49%, 4.95%, 4.91% and 10.86% for $C_7H_{14}NNa_2O_6P$.

EXAMPLE 5

To a slurry of 16.9 grams (0.1 mole) of N-phosphonomethylglycine in 50 ml. of water is added 16 grams (0.2 mole) of 50% aqueous sodium hydroxide. The hot solution is stirred and cooled to 35° C. in a flask equipped with a pressure-equalized dropping funnel and a dry-ice condenser vented to the atmosphere. To this solution is added 6.0 grams (0.1+ mole) of propylene oxide. The solution is stirred overnight. To complete the reaction, a 2.0 gram portion of propylene oxide is added, and the solution is stirred and allowed to stand for several days. The solution is then rotoevaporated to dryness, and the solid is redried over pellets of potassium hydroxide. The product, obtained as a brittle white foamed solid, is the disodium salt of N-(2-hydroxy-1-propyl)-N-phosphonomethylglycine. Elemental analysis shows 27.54% carbon, 4.63% hydrogen and 10.38% phosphorus as against calculated values of 26.58%, 4.46% and 11.42% for $C_6H_{12}NNa_2O_6P$.

EXAMPLE 6

To a solution of the disodium salt of N-phosphonomethylglycine, produced as in Example 1 above, is added 5.0 grams (0.1 mole) of ethylene oxide through a dry-ice condenser. The solution is allowed to stir overnight in a melting icebath and to stand for several days. To complete the reaction, successive 0.5 and 1.0 gram portions of ethylene oxide are added, allowing overnight reaction periods after each addition. The solutions is then rotoevaporated to dryness, and the solid is redried over potassium hydroxide pellets. The product, obtained as a brittle white foam, is the disodium salt of N-(2-hydroxyethyl)-N-phosphonomethylglycine. Elemental analysis shows 22.96% carbon, 4.27% hydrogen and 11.31% phosphorus as against calculated values of 23.36%, 3.92% and 12.05% for $C_5H_{10}NNa_2O_6P$.

EXAMPLE 7

A solution of the disodium salt of N-phosphonomethylglycine is prepared as in Example 1. To 27.5 grams (0.0437 mole) of the solution is added 5.1 grams (0.05 mole) of ethyl glycidyl ether. The solution is diluted with 30 ml. water and 1 drop of Aliquat 336 phase-transfer catalyst solution is added. It is then rotated on a polymer wheel for 5 days, treated with 1.0 gram of ethyl glycidyl ether, rotated for 10 days, then warmed with charcoal and filtered to remove resinous material. The solution is then rotoevaporated to dryness, and the solid is redried over potassium hydroxide pellets at 100° C. and <1 mm. Hg. The product, obtained as a tan, brittle foamed glass, is the disodium salt of N-(3-ethoxy-2-hydroxy-1-propyl)-N-phosphonomethylglycine. Elemental analysis shows 31.15% carbon, 5.62% hydrogen and 8.87% phosphorus as against calculated values of 30.49%, 5.12% and 9.83% for $C_8H_{16}NNa_2O_7P$.

EXAMPLE 8

To a solution of 0.05 mole of the product of Example 5 above, is added 11.3 grams (0.1 mole) of 30% hydrogen peroxide. The solution is left standing for several days, then heated overnight at 40°-45° C. It is rotoevaporated to dryness at 40°-45° C. and <1 mm. Hg. and redried over potassium hydroxide for several days. The product, obtained as a brittle white foam, is the disodium salt of N-(2-hydroxypropyl)-N-phosphonomethylglycine,N-oxide.

EXAMPLE 9

To a solution of 0.05 mole of the product of Example 6 above, is added 11.3 grams (0.1 mole) of 30% hydrogen peroxide. The solution is left standing for three days at 20°-25° C., then heated overnight in an oven at 40°-45° C. It is rotoevaporated to dryness at 40°-45° C., and the solid is redried in vacuo over potassium hydroxide pellets for several days. The product, obtained as a brittle white foam, is the disodium salt of N-(2-hydroxyethyl)-N-phosphonomethylglycine,N-oxide.

EXAMPLE 10

To a solution of 10.0 grams of the product of Example 1 in 30 ml. of water, there is added 6.8 grams of 30% hydrogen peroxide. The solution is allowed to stand for a day at 20°-25° C., then heated overnight in an oven at 45° C., and finally rotoevaporated to dryness at a temperature below 50° C. The solid is redried in vacuo over potassium hydroxide pellets. The product, obtained as a brittle white foam, is the disodium salt of N-(2,3-dihydroxy-1-propyl)-N-phosphonomethylglycine,N-oxide.

EXAMPLE 11

To a solution of 10.0 grams of the product of Example 2 in 30 ml. of water, there is added 7.5 grams of 30% hydrogen peroxide. The solution is allowed to stand for a day at 20°-25° C., then heated overnight in an oven at 45° C., rotoevaporated to dryness at a temperature below 50° C., and the solid is redried in vacuo over potassium hydroxide pellets. The product, obtained as a brittle white foam, is the tetrasodium salt of N,N'-di(carboxymethyl)-N,N'-di(phosphonomethyl)-1,3-diamino-2-propanol,N,N'-dioxide.

In determining the appropriate rates and time of application to sugarcane plants, it is necessary to consider both the chronological age of the plant and its stage of maturity since cane, depending upon the practice in different geographical areas, is grown from 9 to about 30 months before harvest. Application at a rate of from about 0.11 to 5.6 kg. per hectare can be made from about 2 to 10 weeks prior to the projected harvest date. Preferably, such applications are made from 3 to 7 weeks before said date.

The active ingredients of this invention can be conveniently applied to the plants as an aqueous solution or suspension. The active ingredient can, of course, be in its free acid form although it may be employed in the form of any of the above-defined salts in order to improve such ancillary features as solubility or stability. For example, a liquid composition may be applied from a boom-spray, or a solid dust composition where the active component is diluted with an insert such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkylphenoxypoly(ethyleneoxy)ethanols, ployethylene oxide adducts of fatty and resin acids, and long chain alkyl mercaptan adducts with ethylene oxide.

A particularly preferred carrier for the acids or salts of this invention is water with about 0.1 to 2.0% by weight of surfactant added thereto. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific test data which follows are presented as illustrative, non-limiting demonstrations of the useful and unexpected properties of the acids and salts of this invention.

One-half gram of a compound of this invention is dissolved in 4 ml. water that contains as a surfactant about 0.25% (w./w.) nonylphenol which was ethoxylated to contain about 10.5 mols. of ethylene oxide per mol. of nonylphenol ("Tergitol NPX"). 0.6 ml. of this solution is deposited or dropped by means of a syringe with a fine needle on the spindle area at the top of the last visible dewlap of each of 20 stalks of sugarcane. (A dewlap is the junction between the blade of the leaf and the sheath which clasps the stalk). Ten of these stalks were harvested 4 weeks after such treatment and 10 more were harvested 5 weeks after such treatment.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugarcane. The results are given below:

|  | FOUR WEEKS | | FIVE WEEKS | |
|---|---|---|---|---|
|  | Juice Purity | Pol % Cane | Juice Purity | Pol % Cane |
| Control | 67.7 | 6.8 | 75.7 | 9.3 |

-continued

|  | FOUR WEEKS | | FIVE WEEKS | |
|---|---|---|---|---|
|  | Juice Purity | Pol % Cane | Juice Purity | Pol % Cane |
| (untreated) | | | | |
| Example 5 | 73.0 | 7.8 | 73.4 | 8.3 |
| Example 6 | 71.5 | 7.6 | 84.9 | 12.0 |

The treated plants clearly demonstrated a substantial increase in both of the factors measured at the earlier harvest date. The same is true for the compound of Example 6 at the later harvest date.

In selecting compounds of the present invention for treatment of sugarcane plants, it is preferred to employ those wherein $x$, $y$ and $z$ are each one. Within this group, the dialkali metal salts wherein R is hydrogen or methyl are particularly preferred.

Although the invention has been described herein with respect to specific embodiments, the details thereof are not to be construed as limitations except to the extent defined in the following claims.

What is claimed is:

1. A method for increasing the sucrose content of sugarcane plants which comprises applying to said plants, from about 2 to 10 weeks prior to harvest, an effective sucrose increasing amount of a compound of the formula

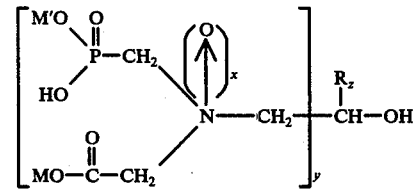

wherein $x$ is selected from zero and one, $y$ is selected from one and two, $z$ is selected from zero and one, the sum of $y + z$ is two, R is selected from hydrogen, methyl, ethyl, hydroxymethyl and lower alkoxymethyl, M is selected from hydrogen, lower alkyl and alkali metal, and M' is selected from hydrogen, lower alkyl, phenyl and alkali metal.

2. A method as defined in claim 1 wherein application is at a rate of about 0.11 to 5.6 kg. per hectare.

3. A method as defined in claim 1 wherein application is made from about 3 to 7 weeks prior to harvest.

4. A method as defined in claim 1 wherein $x$, $y$ and $z$ are each one.

5. A method as defined in claim 4 wherein M and M' are each alkali metal.

6. A method as defined n claim 5 wherein R is hydrogen.

7. A method as defined in claim 5 wherein R is methyl.

8. A method as defined in claim 5 wherein M and M' are each sodium.

9. A method as defined in claim 5 wherein application is at a rate of about 0.11 to 5.6 kg. per hectare.

10. A method as defined in claim 5 wherein application is made from about 3 to 7 weeks prior to harvest.

11. A method as defined in claim 1 wherein $y$ is two and $z$ is zero.

* * * * *